United States Patent
Egi et al.

(10) Patent No.: US 11,551,818 B2
(45) Date of Patent: Jan. 10, 2023

(54) COMPUTER SYSTEM AND METHOD OF PRESENTING INFORMATION RELATED TO BASIS OF PREDICTED VALUE OUTPUT BY PREDICTOR

(71) Applicant: Hitachi, Ltd., Tokyo (JP)

(72) Inventors: Masashi Egi, Tokyo (JP); Yuxin Liang, Tokyo (JP); Naoaki Yokoi, Tokyo (JP); Masayoshi Mase, Tokyo (JP); Naofumi Hama, Tokyo (JP); Yasuhide Mori, Tokyo (JP); Hiroyuki Namba, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 855 days.

(21) Appl. No.: 16/504,897

(22) Filed: Jul. 8, 2019

(65) Prior Publication Data
US 2020/0034738 A1 Jan. 30, 2020

(30) Foreign Application Priority Data
Jul. 27, 2018 (JP) .............................. JP2018-141375

(51) Int. Cl.
*G06N 20/00* (2019.01)
*G16H 50/70* (2018.01)
(Continued)

(52) U.S. Cl.
CPC ......... *G16H 50/70* (2018.01); *G06F 16/2272* (2019.01); *G06N 5/02* (2013.01);
(Continued)

(58) Field of Classification Search
None
See application file for complete search history.

(56) References Cited

U.S. PATENT DOCUMENTS

| 10,510,022 B1 * | 12/2019 | Tharrington, Jr. ..... G06N 5/045 |
| 2016/0253467 A1 | 9/2016 | Kitagawa et al. |
| 2018/0158552 A1 | 6/2018 | Liu et al. |

FOREIGN PATENT DOCUMENTS

JP 2016-162131 A 9/2016

OTHER PUBLICATIONS

Ribeiro et al., "'Why Should I Trust You?' Explaining the Predictions of Any Classifier", KDD, 2016, San Francisco, CA, (10 pages).

(Continued)

*Primary Examiner* — Ryan Barrett
(74) *Attorney, Agent, or Firm* — Crowell & Moring LLP

(57) ABSTRACT

There is provided is a computer system that outputs a predicted value of data to be evaluated using a predictor generated using learning data. The computer system includes the predictor; an index calculation unit that calculates an interpretation index of the data to be evaluated; and an extraction unit that selects the learning data useful for a user to interpret the predicted value of the data to be evaluated, wherein index management information for managing an interpretation index of the learning data is stored, the index calculation unit calculates the interpretation index of the data to be evaluated, and the extraction unit calculates a selection index based on the interpretation index of the data to be evaluated and the interpretation index of the learning data, selects the learning data based on the selection index, and outputs display information for presenting information indicating a processing result.

12 Claims, 14 Drawing Sheets

(51) Int. Cl.
*G06F 16/22* (2019.01)
*G06N 5/04* (2006.01)
*G06N 5/02* (2006.01)

(52) U.S. Cl.
CPC ............... *G06N 5/04* (2013.01); *G06N 5/045* (2013.01); *G06N 20/00* (2019.01)

(56) References Cited

OTHER PUBLICATIONS

Lundberg et al., "A Unified Approach to Interpreting Model Predictions", 31st Conference on Neural Information Processing Systems, 2017, pp. 1-10, Long Beach, CA, (10 pages).
Extended European Search Report issued in counterpart European Application No. 19188123.4 dated Jan. 3, 2020 (nine (9) pages).

* cited by examiner

| ID | FEATURE | | | | CORRECT ANSWER VALUE | PREDICTED VALUE |
|---|---|---|---|---|---|---|
| | GENDER | AGE | ... | OCCUPATION | | |
| 1 | V_11 | V_12 | ... | V_1N | +23 | +22.5 |
| 2 | V_21 | V_22 | ... | V_2N | +18 | +17.9 |
| ⋮ | ⋮ | ⋮ | ⋮ | ... | ⋮ | ⋮ |
| M | V_M1 | V_M2 | ... | V_MN | +5 | +5.1 |

| ID | CONTRIBUTION DEGREE | | | | CORRECT ANSWER VALUE | PREDICTED VALUE |
|---|---|---|---|---|---|---|
| | GENDER | AGE | ... | OCCUPATION | | |
| 1 | +17 | +4 | ... | +12 | +23 | +22.5 |
| 2 | -6 | -3 | ... | +6 | +18 | +17.9 |
| ⋮ | ⋮ | ⋮ | ⋮ | ... | ⋮ | ⋮ |
| M | +47 | -56 | ... | -19 | +5 | +5.1 |

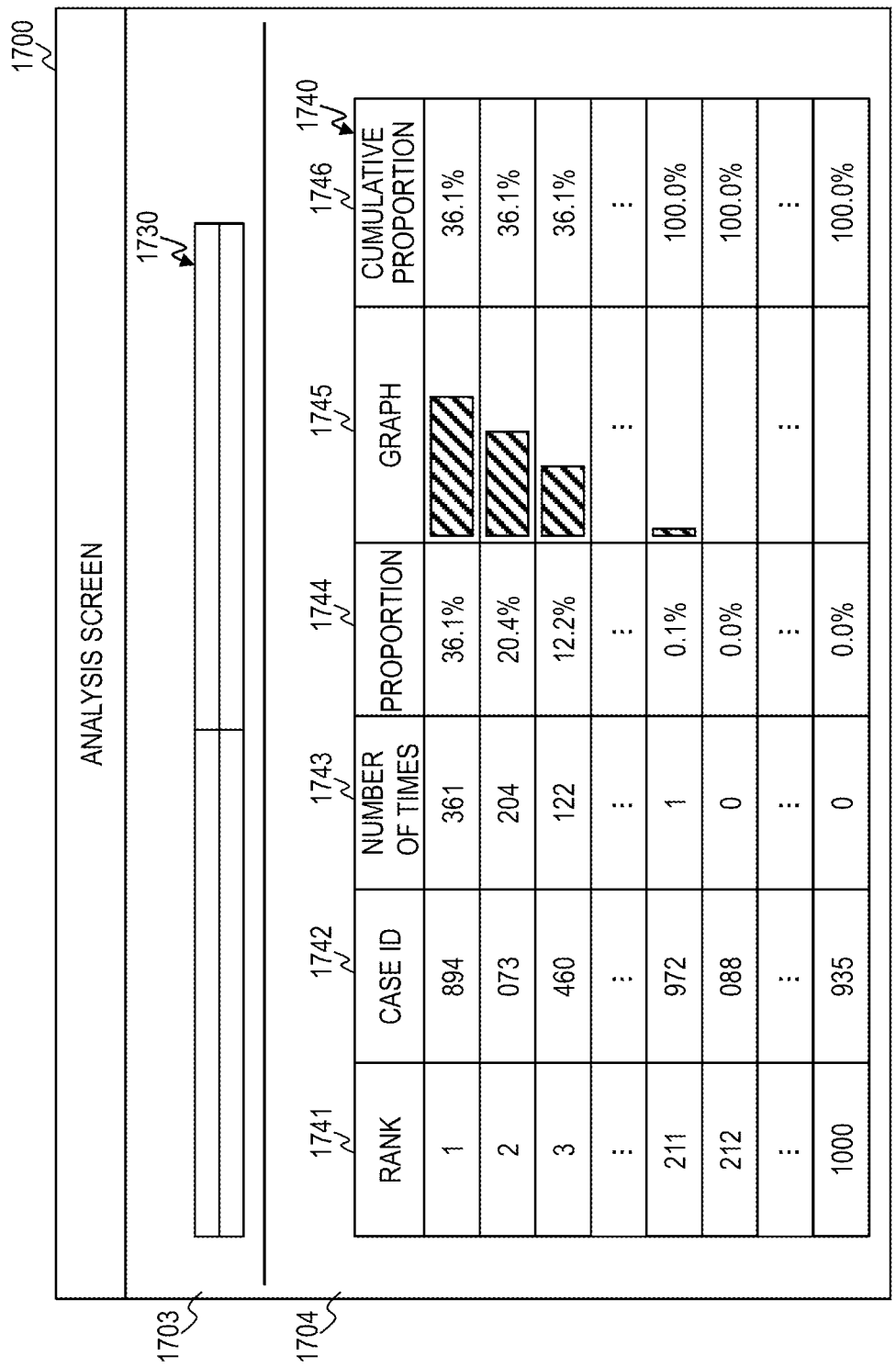

COMPUTER SYSTEM AND METHOD OF PRESENTING INFORMATION RELATED TO BASIS OF PREDICTED VALUE OUTPUT BY PREDICTOR

CLAIM OF PRIORITY

The present application claims priority from Japanese patent application JP 2018-141375 filed on Jul. 27, 2018, the content of which is hereby incorporated by reference into this application.

BACKGROUND OF THE INVENTION

The present invention relates to a system and a method that presents useful data for interpreting a prediction basis of AI.

In recent years, support systems utilizing AI in various fields such as medical care and finance have been provided. For example, in the medical field, AI is utilized to predict the morbidity of a disease, identify symptoms, and the like. In the financial field, AI is utilized to perform credit screening and the like.

As a result of an advance in technological development aiming at improving the accuracy of prediction output by AI, such as prediction of the morbidity of a disease, the black-box processing of an AI model (algorithm) is accelerated. Therefore, there is a problem that a user who uses AI cannot trust a predicted value of AI.

Under such a background, there is an increasing demand for explaining a prediction basis of AI and verifying an operation by a developer or an operator of a system utilizing AI.

Techniques disclosed in Patent Literature 1 (JP-A-2016-162131) and Non-Patent Literature 1 (Marco Tulio Ribeiro, etc. "Why Should I Trust You?": Explaining the Predictions of Any Classifier, KDD'16 Proceedings of the 22nd ACM SIGKDD International Conference on Knowledge Discovery and Data Mining, August 2016, Pages 1135 to 1144.) are known as techniques for presenting information indicating the reliability of a system to a user who uses the system.

Patent Literature 1 describes "Medical care data display screen displays diagnostic support information calculated by a diagnostic support program. The diagnosis support program calculates the diagnosis support information by performing an operation using a plurality of items of patient medical care data as input items. In addition to the diagnosis support information, contribution information is displayed on the medical care data display screen. The contribution information is information including, among the plurality of the input items, an item of which contribution degree to the diagnosis support information, which is a calculation result, exceeds a predetermined value."

Non-Patent Literature 1 and Non-Patent Literature 2 (Scott M Lundberg et, "A Unified Approach to Interpreting Model Predictions", Advances in Neural Information Processing Systems 30, December 2017, Pages 4765 to 4774.) describe data calculation methods that use a combination of a plurality of perturbation data generated by changing data to be evaluated and predicted values obtained by inputting the perturbation data to AI to explain a prediction basis of AI for the data to be evaluated.

The contribution degree disclosed in Patent Literature is calculated based on the similarity of values of examination data items. However, AI does not necessarily predict based on the similarity of the item values. For example, high prediction accuracy can be achieved by predicting based on a combination of a plurality of items. Therefore, the technique disclosed in Patent Literature 1 cannot be applied to such AI. In addition, there is a problem that the user lacks persuasiveness if only outputting data calculated using the techniques described in Non-Patent Literature 1 and Non-Patent Literature 2 as information for interpreting a prediction basis.

SUMMARY OF THE INVENTION

The invention provides a method and a system for outputting data useful for a user to interpret a prediction basis of AI.

A representative example of the invention disclosed in this application is a computer system that outputs a predicted value of data to be evaluated composed of a plurality of features using a predictor generated using a plurality of pieces of learning data composed of the plurality of features and correct answer values, being composed of at least one computer having a processor, a memory connected to the processor, and a network interface connected to the processor, and including the predictor; an index calculation unit that calculates a first interpretation index configured to interpret the predicted value of the data to be evaluated output by the predictor; and an extraction unit that calculates a selection index configured to select the learning data useful for a user to interpret the predicted value of the data to be evaluated, and selects the learning data based on the selection index. Index management information configured to manage a second interpretation index configured to interpret the correct answer value included in the learning data is stored; the predictor outputs the predicted value of the data to be evaluated; the index calculation unit calculates the first interpretation index based on the predicted value of the data to be evaluated and the data to be evaluated; and the extraction unit calculates the selection index based on the first interpretation index and the second interpretation index, selects the learning data based on the selection index, generates display information configured to present information on the interpretation index of the data to be evaluated and the selected learning data, and outputs the display information.

According to the invention, it is possible to output the data useful for the user to interpret the prediction basis of a predictor (AI). Problems, configurations, and effects other than those described above will be clarified by the descriptions of the following embodiments.

BRIEF DESCRIPTION OF THE DRAWINGS

FIG. 17C shows an example of an analysis screen displayed on the terminal according to the third embodiment.

DESCRIPTION OF EMBODIMENTS

Figure 1:
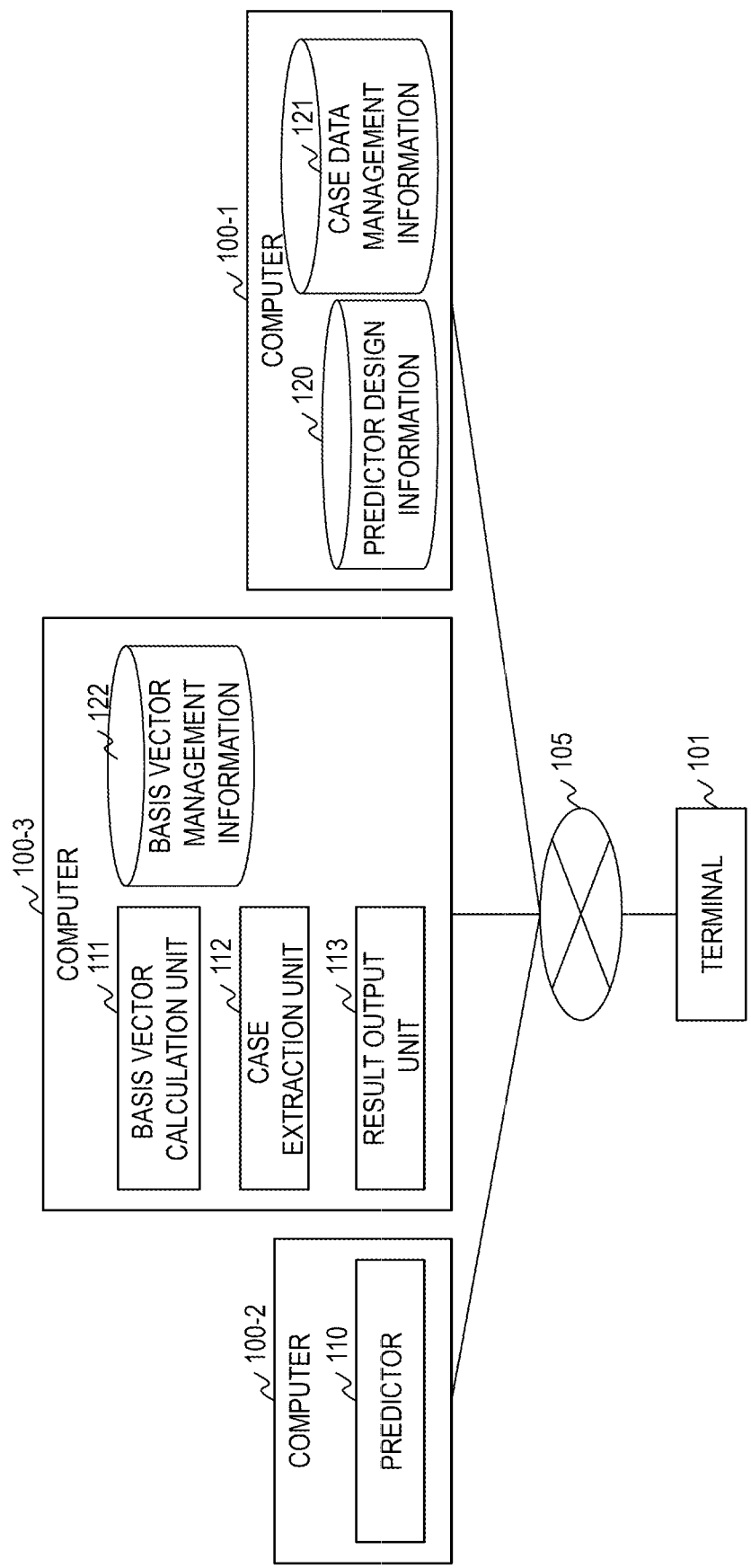
FIG. 1 shows a configuration example of a computer system according to a first embodiment.

Embodiments of the invention will be described below using the drawings. However, the invention is not to be constructed as being limited to the description content in the embodiment described hereinafter. It will be understood by those skilled in the art that the detailed configuration of the invention can be changed without departing from the scope and spirit of the invention.

In configurations of the invention described below, the same or similar configurations or functions are denoted by the same reference numerals, and a repeated description thereof is omitted.

Terms such as "first", "second", "third" in the present specification are used to identify constituent elements and do not necessarily limit the number or order.

The position, size, shape, range, and the like of respective components shown in the drawings may not represent the actual position, size, shape, range, and the like in order to facilitate understanding of the invention. Therefore, the invention is not limited to the position, size, shape, and range disclosed in the drawings.

First Embodiment

FIG. 1 shows a configuration example of a computer system according to the first embodiment.

The computer system includes a plurality of computers 100-1, 100-2, 100-3, and a terminal 101. The plurality of computers 100-1, 100-2, 100-3 and the terminal 101 are connected to each other via a network 105. The network 105 is, for example, a Wide Area Network (WAN) and a Local Area Network (LAN). The connection method of the network 105 may be either wired or wireless.

In the following description, when the computers 100-1, 100-2, and 100-3 are not distinguished from others, they are described as a computer 100.

The terminal 101 is a computer operated by a user. The terminal 101 is, for example, a personal computer, a smartphone, a tablet terminal, or the like. The terminal 101, based on a user's operation, inputs data (data to be evaluated) and the like necessary for a prediction made by AI. The data to be evaluated includes values (features) of a plurality of items.

The terminal 101 includes a processor, a memory, a network interface, an input device, and an output device. The input device is a device such as a keyboard, a mouse, and a touch panel, and the output device is a device such as a touch panel and a display.

The computer 100-1 manages various types of data. Specifically, the computer 100-1 holds predictor design information 120 and case data management information 121.

The predictor design information 120 is definition information of a predictor 110. For example, the predictor design information 120 is definition information related to nodes of a hierarchy in a neural network and connections between nodes of each hierarchy. The case data management information 121 is information for managing learning data. The learning data of the present embodiment is data generated based on past cases. In the following description, the learning data is also described as case data.

The computer 100-2 is a computer that predicts, based on an arbitrary model (algorithm), the data to be evaluated and outputs a predicted value. The prediction for the data to be evaluated is, for example, classification of the data to be evaluated and prediction of an arbitrary event, and the like. The computer 100-2 includes a predictor 110 that predicts the data to be evaluated.

The computer 100-3 is a computer that outputs information for the user to interpret a prediction basis for the data to be evaluated. In the following description, the information for the user to interpret the prediction basis is also described as interpretation information. The computer 100-3 includes a basis vector calculation unit 111, a case extraction unit 112, and a result output unit 113 and holds basis vector management information 122.

The basis vector calculation unit 111 calculates a basis vector serving as an index for interpreting the prediction for the data to be evaluated. The component of the basis vector is a contribution degree to the predicted values of features constituting data input to the predictor 110.

The case extraction unit 112 selects, from the case data, the case data useful for the user to interpret the predicted value of the data to be evaluated, based on a selection index calculated using the basis vector. The selection index is an index for selecting the case data having an arbitrary relationship with the data to be evaluated.

The result output unit 113 generates display data including the predicted value of the data to be evaluated and the interpretation information, and transmits the display data to the terminal 101. The interpretation information includes the basis vector of the data to be evaluated, the selected case data, and the like.

Note that any one of the computers 100-1, 100-2, and 100-3 includes an operation receiving unit that provides an Application Programming Interface (API) for receiving a request from the terminal 101.

Figures 2, 3, 4:
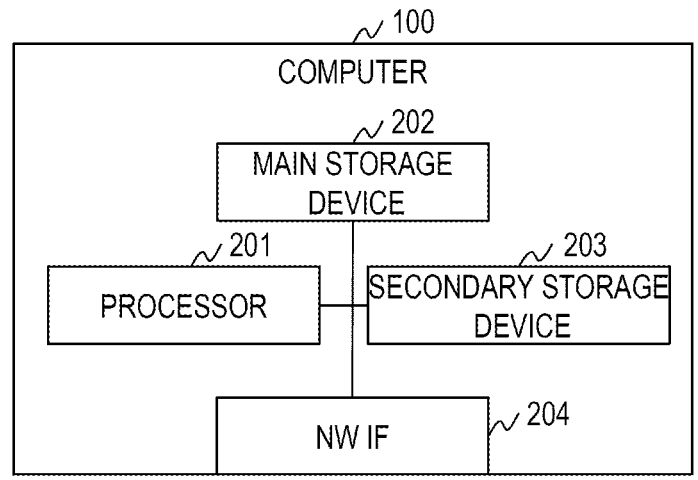
FIG. 2 shows an example of a hardware configuration of a computer according to the first embodiment.
FIG. 3 shows an example of a data structure of case data management information according to the first embodiment.
FIG. 4 shows an example of a data structure of basis vector management information according to the first embodiment.

Here, a hardware configuration of the computer 100 will be described. FIG. 2 shows an example of the hardware configuration of the computer 100 according to the first embodiment.

The computer 100 includes a processor 201, a main storage device 202, a secondary storage device 203, and a network interface 204. The respective pieces of hardware are connected to each other via an internal bus. The computer 100 may not include the secondary storage device 203. Further, the computer 100 may include an input device and an output device.

The processor 201 executes a program stored in the main storage device 202. The processor 201 executes processing in accordance with the program, thereby operating as a functional unit (module) that realizes a specific function such as the basis vector calculation unit 111. In the following description, when processing is described with the functional unit as the subject, it is indicated that the processor 201 is executing a program for realizing the functional unit.

The main storage device 202 stores the program executed by the processor 201 and information used by the program. The main storage device 202 includes a work area temporarily used by the program.

A program for realizing a data management unit (not shown) is stored in the main storage device 202 of the computer 100-1. A program for realizing the predictor 110 is stored in the main memory 202 of the computer 100-2. A program for realizing the basis vector calculation unit 111, the case extraction unit 112, and the result output unit 113 is stored in the main storage device 202 of the computer 100-3. Further, a program for realizing the operation receiving unit is stored in the main storage device 202 of any of the computers 100-1, 100-2, and 100-3.

The secondary storage device 203, such as a Hard Disk Drive (HDD) and a Solid State Drive (SSD), stores data permanently.

The secondary storage device 203 of the computer 100-1 stores the predictor design information 120 and the case data management information 121. The secondary storage device 203 of the computer 100-3 stores the basis vector management information 122.

For the functional units included in each computer 100, the plurality of functional units may be integrated into one functional unit, or one functional unit may be divided into a plurality of functional units by each function.

FIG. 3 shows an example of a data structure of the case data management information 121 according to the first embodiment.

The case data management information 121 stores a plurality of entries which are an ID 301, a feature 302, a correct answer value 303, and a predicted value 304. One entry corresponds to one piece of the case data. The case data includes a plurality of features and a correct answer value.

The ID 301 is a field for storing identification information of the case data. In the ID 301 according to the first embodiment, a number is stored.

The feature 302 is a field group that stores features which are values of items constituting the case data. The items include, for example, gender, age, heart rate, and deposit amount. Any one of "male" and "female" is stored as the feature in the field of the item corresponding to the gender, and a numerical value is stored as the feature in the field of the item corresponding to the age.

The correct answer value 303 is a field for storing the correct values constituting the case data. The values stored in the correct answer value 303 are given in advance. The predicted value 304 is a field for storing predicted values calculated by the predictor 110 according to the feature 302 with respect to the correct answer value 303. Although the values stored in the predicted value 304 are given in advance in this embodiment, when the values of the predicted value 304 are not given in advance, the values calculated by inputting the values of the feature 302 to the predictor 110 may be set as the predicted value 304.

In the invention, the predictor 110 can calculate the predicted value 304 with respect to the correct answer value 303 according to the feature 302 in a sufficient accuracy, and the contribution degree of each item to the correct value 303 can be sufficiently approximated by the contribution degree to the predicted value 304.

As an example of the present embodiment, a regression problem is described in which a predicted value composed of one numerical value is calculated with respect to a correct answer value composed of one numerical value, but the invention is not limited to this. For example, even an identification problem in which a probability value of a plurality of labels which are answer candidates is calculated with respect to a correct answer value composed of one label can be easily extended.

FIG. 4 shows an example of a data structure of the basis vector management information 122 according to the first embodiment.

The basis vector management information 122 stores a plurality of entries which are an ID 401, a contribution degree 402, a correct answer value 403, and a predicted value 404. One entry corresponds to a basis vector of one piece of the case data. The ID 401, the correct answer value 403, and the predicted value 404 are the same fields as the ID 301, the correct answer value 303, and the predicted value 304.

The contribution degree 402 is a field group that stores contribution degrees indicating the extent of the contribution of the feature of each item to the predicted value. In the first embodiment, a vector with values of each field included in the contribution degree 402 as components is treated as a basis vector.

Figure 5:
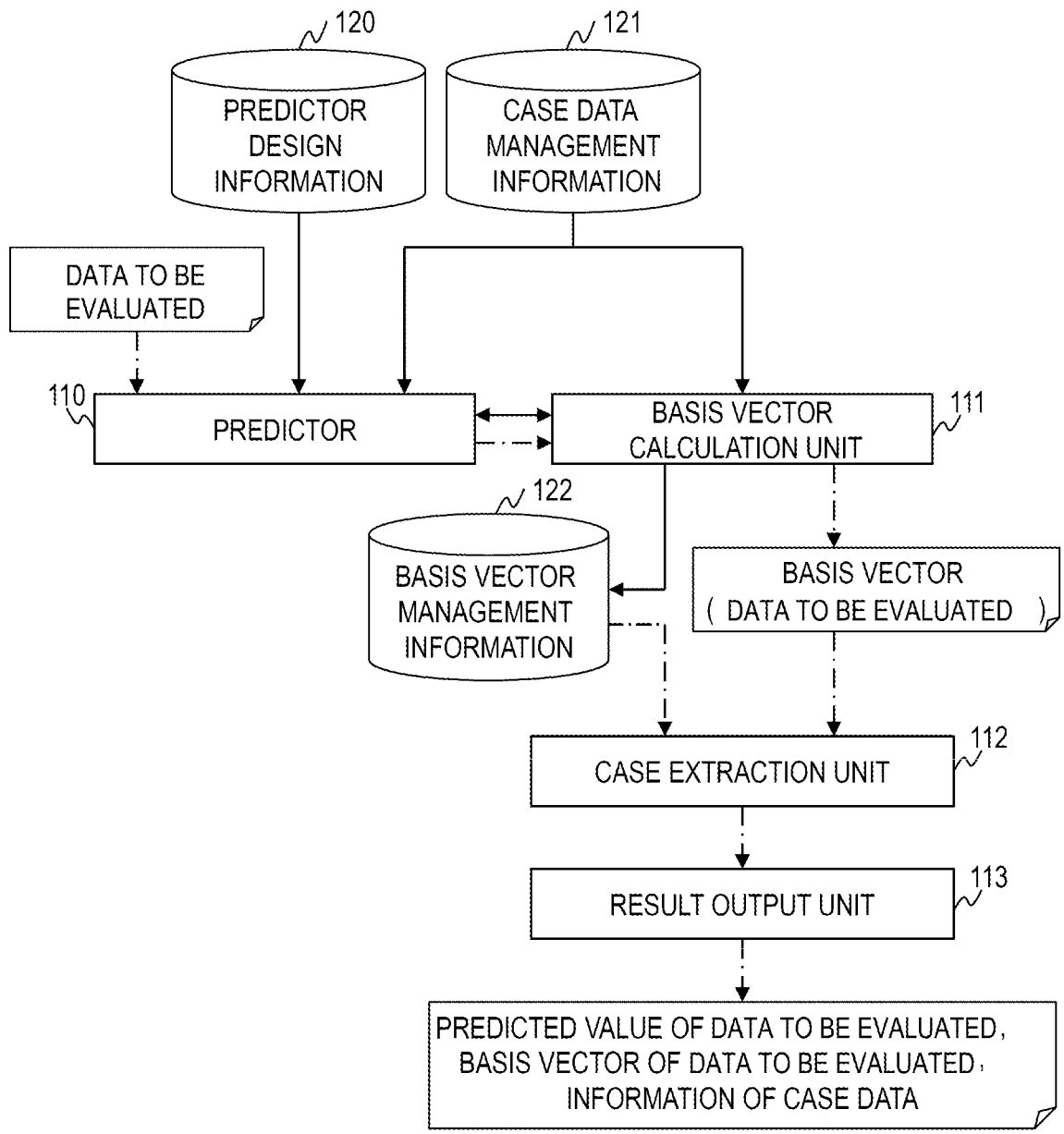
FIG. 5 shows a processing flow of the computer system according to the first embodiment.

FIG. 5 shows a processing flow of the computer system according to the first embodiment.

Arrows in the drawing indicate the flow of data. A solid line indicates the flow of data in the processing for generating the basis vector of the case data. A dashed-dotted line indicates the flow of data in the processing for outputting the predicted value of the data to be evaluated and the interpretation information.

First, the flow of processing for calculating the basis vector of the case data will be described.

Upon receiving a generation request of the predictor 110 from the terminal 101, the operation receiving unit outputs a generation instruction of the predictor 110 to the computer 100-2. Upon receiving a generation request of the basis vector of the case data from the terminal 101, the operation receiving unit outputs a calculation instruction of the basis vector of the case data to the computer 100-3.

Upon receiving the generation instruction of the predictor 110, the computer 100-2 generates the predictor 110 from the predictor design information 120. If the predictor 110 has already been generated, the processing can be omitted.

Upon receiving the generation instruction of the basis vector of the case data, the basis vector calculation unit 111 of the computer 100-3 calculates the basis vector of each case data stored in the case data management information 121. The basis vector calculation unit 111 registers the calculated basis vector of the case data in the basis vector management information 122.

Next, the flow of processing for outputting the predicted values of the data to be evaluated and the interpretation information will be described.

Upon receiving a prediction request including the data to be evaluated from the terminal 101, the operation receiving unit outputs a prediction instruction of the data to be evaluated to the computer 100-2, and outputs a selection instruction of the case data to the computer 100-3.

Upon receiving the prediction instruction of the data to be evaluated, the predictor 110 of the computer 100-2 predicts the data to be evaluated, and outputs the data to be evaluated and the predicted values to the basis vector calculation unit 111.

Upon receiving the selection instruction of the case data, the basis vector calculation unit 111 of the computer 100-3 calculates the basis vector of the data to be evaluated based on the data to be evaluated and the predicted values input from the predictor 110. The basis vector calculation unit 111 outputs the combination of the basis vector of the data to be evaluated and the predicted values to the case extraction unit 112.

The case extraction unit 112 of the computer 100-3 selects the case data based on the basis vector of the data to be evaluated and the selection index calculated by using the basis vectors of the case data. The case extraction unit 112 outputs the information on the selected case data and the combination of the basis vector of the data to be evaluated and the predicted values to the result output unit 113. The information on the selected case data includes, for example, the basis vector of the case data.

The result output unit 113 of the computer 100-3 generates display information for displaying the information input from the case extraction unit 112. The result output unit 113 outputs the display information to the operation receiving unit. The operation receiving unit transmits the display information to the terminal 101.

The basis vector is an index for interpreting the basis of the prediction performed by the predictor 110 on the data to be evaluated. Therefore, the selection index calculated based on the basis vector can be treated as an index reflecting the characteristics of a model of the predictor 110. As a result, the case data selected based on the selection index has an arbitrary relationship with the data to be evaluated in the prediction of the predictor 110. Thus, since the case data selected based on the selection index is the data selected based on a viewpoint (index) different from that of the case data selected based on the relationship between the data to be evaluated and the case data, the case data selected based on the selection index is considered to be useful as information for interpreting the predicted values of the data to be evaluated.

For example, the case data corresponding to the basis vector similar to the basis vector of the data to be evaluated may be a predicted value similar to the predicted value of the data to be evaluated. In addition, the case data corresponding to the basis vector of the feature in contrast with the basis vector of the data to be evaluated may be a predicted value different from the predicted value of the data to be evaluated.

As described above, by referring to the above-described case data together with the predicted values of the data to be evaluated, the user can interpret the predicted values of the data to be evaluated with a feeling of conviction.

In the first embodiment, the case extraction unit 112 selects the case data based on the selection index indicating the similarity between the basis vectors. The processing for selecting the case data based on the selection index indicating the difference between the basis vectors will be described in the second embodiment.

Next, specific processing contents will be described. First, processing for generating the basis vector of the case data will be described.

Figure 6:
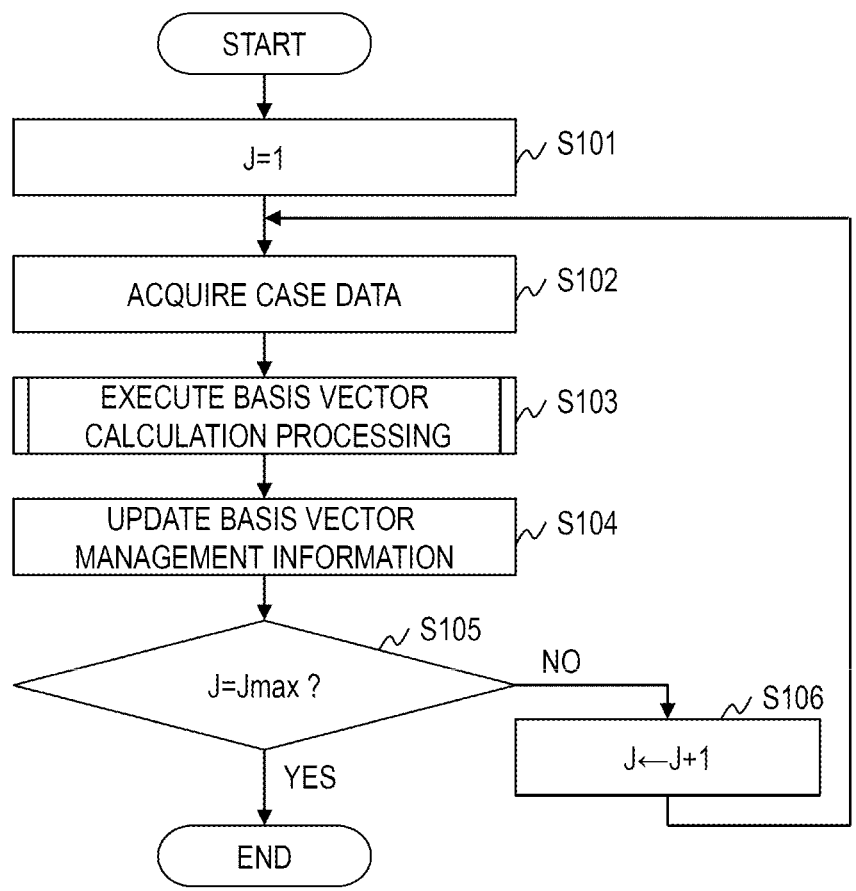
FIG. 6 is a flowchart showing an example of generation processing of the basis vector management information executed by a basis vector calculation unit according to the first embodiment.

FIG. 6 is a flowchart showing an example of generation processing of the basis vector management information 122 executed by the basis vector calculation unit 111 according to the first embodiment.

The basis vector calculation unit 111 sets "1" as the initial value of a variable J (step S101). The variable J is a variable representing the identification number of the case data. At this time, the basis vector calculation unit 111 sets the number of pieces of case data registered in the case data management information 121 as Jmax.

Next, the basis vector calculation unit 111 acquires, from the case data management information 121, the case data (entry) of which the ID 301 is identical to the value of the variable J (step S102).

Next, the basis vector calculation unit 111 executes the basis vector calculation processing using the acquired case data (step S103). The basis vector calculation processing will be described in detail with reference to FIG. 7. By executing the basis vector calculation processing, the basis vector of the case data is calculated.

Next, the basis vector calculation unit 111 updates the basis vector management information 122 (step S104).

Specifically, the basis vector calculation unit 111 adds an entry to the basis vector management information 122, sets the value of the variable J in the ID 401 of the added entry, sets the values of the correct answer value 303 in the correct value 403, and sets the values of the predicted value 304 in the predicted value 404. The basis vector calculation unit 111 sets the contribution degree of each item in the field of the contribution degree 402 of the added entry.

Next, the basis vector calculation unit 111 determines whether the value of the variable J is identical to Jmax (step S105). That is, it is determined whether the basis vectors are generated for all the case data registered in the case data management information 121.

When it is determined that the value of the variable J is not identical to Jmax, the basis vector calculation unit 111 sets a value obtained by adding 1 to the value of the variable J as the variable J (step S106). After that, the processing returns to step S102 and the basis vector calculation unit 111 executes the same processing.

When it is determined that the value of the variable J is identical to Jmax, the basis vector calculation unit 111 ends the processing.

Figure 7:
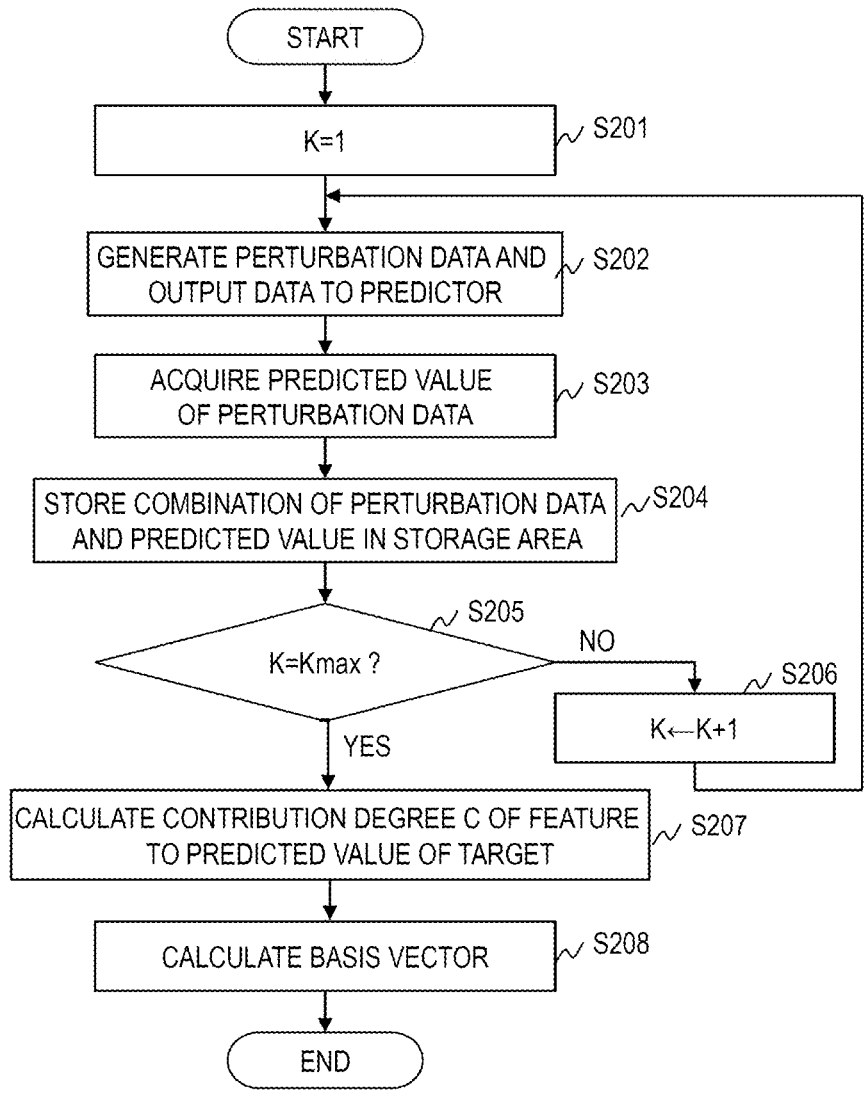
FIG. 7 is a flowchart showing an example of basis vector calculation processing executed by the basis vector calculation unit according to the first embodiment.

FIG. 7 is a flowchart showing an example of basis vector calculation processing executed by the basis vector calculation unit 111 according to the first embodiment.

The basis vector calculation unit 111 executes the following processing for each of the data to be evaluated and the case data. In the following description, when the data to be evaluated and the case data are not distinguished, they are referred to as target data.

The basis vector calculation unit 111 sets "1" as the initial value of a variable K (step S201). The variable K is a variable representing the number of perturbation data to be generated. In the first embodiment, it is assumed that Kmax pieces of perturbation data are generated.

Here, the perturbation data is data in which the features of a part of items of the target data are changed. It is assumed that the change amount is small.

Next, the basis vector calculation unit 111 generates perturbation data of the target data and outputs the generated perturbation data to the predictor 110 (step S202). The basis vector calculation unit 111 enters a waiting state until the predicted value of the perturbation data is output from the predictor 110.

When the predicted value of the perturbation data is acquired from the predictor 110 (step S203), the basis vector calculation unit 111 stores a combination of the perturbation data and the predicted value in a storage area of the main storage device 202 (step S204).

Next, the basis vector calculation unit 111 determines whether the value of the variable K is identical to Kmax (step S205).

When it is determined that the value of the variable K is not identical to Kmax, the basis vector calculation unit 111 sets a value obtained by adding 1 to the value of the variable K as the variable K (step S206). After that, the processing returns to step S202 and the basis vector calculation unit 111 executes the same processing.

When it is determined that the value of the variable K is identical to Kmax, the basis vector calculation unit 111 calculates the contribution degree C_k of the feature of each item to the predicted value of the target data (step S207). Here, C_k represents the contribution degree of the feature of a k-th item to the predicted value of the target data.

Since the contribution degree calculation method is described in Non-Patent Literature 1 and Non-Patent Literature 2, a detailed description thereof is omitted. However, for example, the contribution degree is calculated based on the following processing. The basis vector calculation unit 111 calculates the contribution degree of the feature of each item to the predicted value of the target data by executing statistical analysis such as multiple regression analysis using the combination of the perturbation data and the predicted value.

Next, the basis vector calculation unit 111 calculates the basis vector of the target data with the contribution degree of the feature of each item as a component (step S208).

Next, the processing for outputting the predicted value of the data to be evaluated and the interpretation information will be described.

Figure 8:
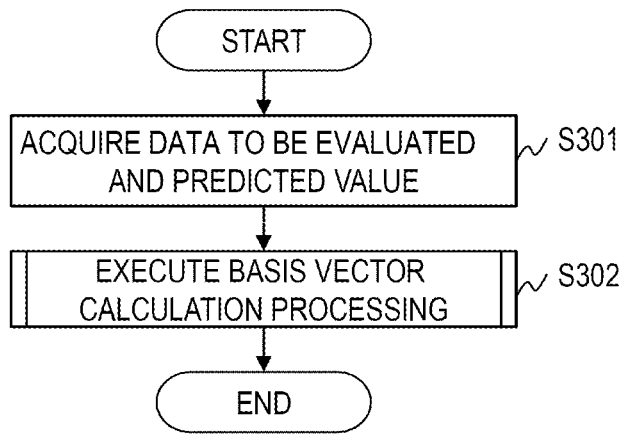
FIG. 8 is a flowchart showing an example of calculation processing of the basis vector of data to be evaluated executed by the basis vector calculation unit according to the first embodiment.

FIG. 8 is a flowchart showing an example of calculation processing of the basis vector of data to be evaluated executed by the basis vector calculation unit 111 according to the first embodiment.

The basis vector calculation unit 111 acquires the data to be evaluated and the predicted value from the predictor 110 (step S301).

The basis vector calculation unit 111 executes the basis vector calculation processing using the data to be evaluated and the predicted value (step S302). The basis vector calculation processing is the same as the processing shown in FIG. 7. By executing the basis vector calculation processing, the basis vector of the data to be evaluated is calculated. The basis vector calculation unit 111 outputs the basis vector of the data to be evaluated to the case extraction unit 112.

Figure 9:
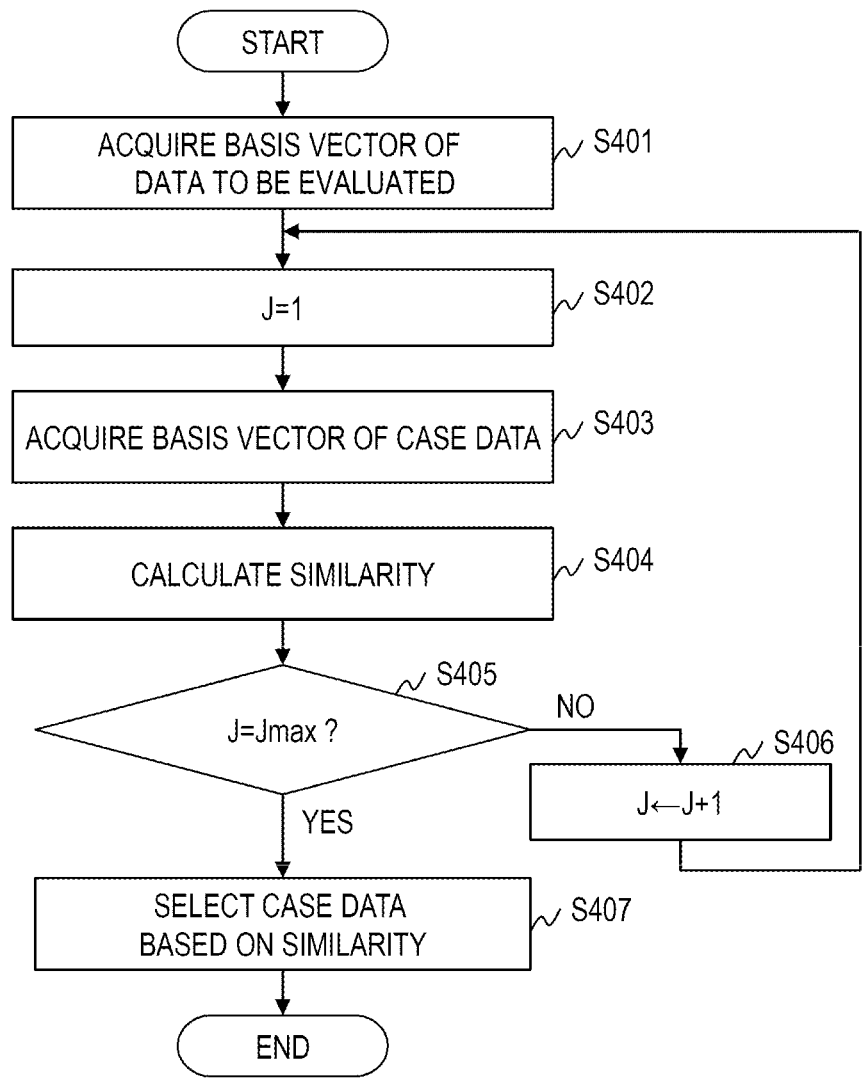
FIG. 9 is a flowchart showing an example of case data selection processing executed by a case extraction unit according to the first embodiment.

FIG. 9 is a flowchart showing an example of the case data selection processing executed by the case extraction unit 112 according to the first embodiment.

The case extraction unit 112 acquires the basis vector of the data to be evaluated from the basis vector calculation unit 111 (step S401).

Next, the case extraction unit 112 sets "1" as the initial value of the variable J (step S402). The variable J is the variable representing the identification number of the case data. At this time, the case extraction unit 112 sets the number of pieces of case data registered in the case data management information 121 as Jmax.

Next, the case extraction unit 112 acquires, from the basis vector management information 122, the basis vector (entry) of the case data of which ID 401 is identical to the value of the variable J (step S403).

Next, the case extraction unit 112 calculates the similarity between the basis vector of the data to be evaluated and the basis vector of the case data (step S404). For example, the case extraction unit 112 calculates the cosine similarity of the two basis vectors. The invention is not limited to the above calculation method of similarity.

Next, the case extraction unit 112 determines whether the value of the variable J is identical to Jmax (step S405). That is, it is determined whether the similarities are calculated for all the case data registered in the case data management information 121.

When it is determined that the value of the variable J is not identical to Jmax, the case extraction unit 112 sets a value obtained by adding 1 to the value of the variable J as the variable J (step S406). Thereafter, the processing returns to step S402 and the case extraction unit 112 executes the same processing.

If it is determined that the value of the variable J is identical to Jmax, the case extraction unit 112 selects the case data based on the similarity (step S407). Thereafter, the case extraction unit 112 ends the processing.

For example, the case extraction unit 112 selects the case data having the highest similarity or the case data having a similarity larger than a threshold value. In addition, the case extraction unit 112 selects a predetermined number of pieces of the case data in descending order of the similarity. The invention is not limited to the method of selecting the case data based on the similarity.

Figure 10:
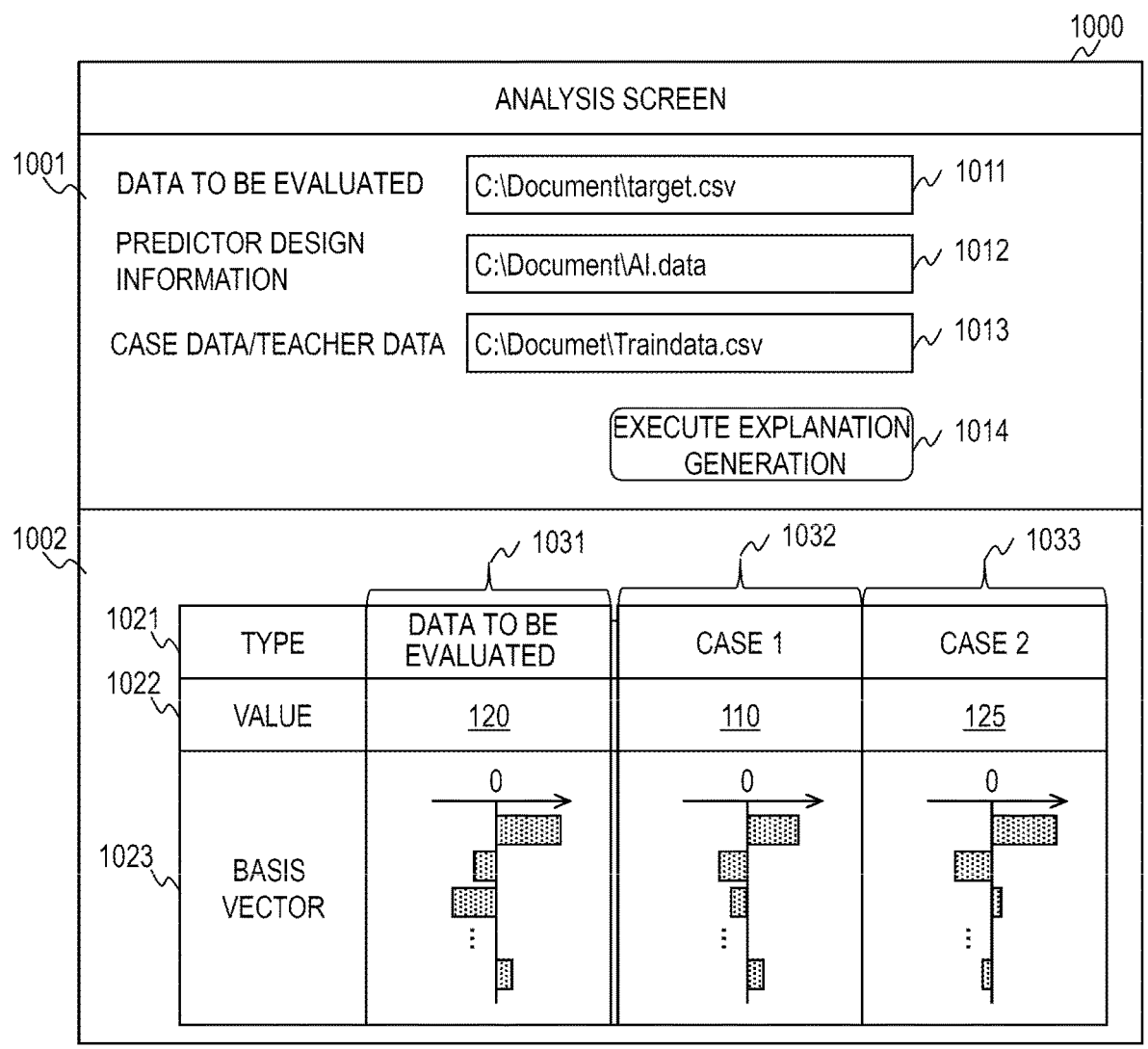
FIG. 10 shows an example of an analysis screen displayed on a terminal according to the first embodiment.

FIG. 10 shows an example of an analysis screen displayed on the terminal 101 according to the first embodiment.

An analysis screen 1000 is provided by the operation receiving unit and is displayed on the terminal 101. The analysis screen 1000 includes a data setting field 1001 and an output field 1002.

The data setting field 1001 includes a first data setting field 1011, a second data setting field 1012, a third data setting field 1013, and an execution button 1014.

The first data setting field 1011 specifies the data to be evaluated. The second data setting field 1012 specifies the predictor design information 120. The third data setting field 1013 specifies the case data management information 121. The execution button 1014 is an operation button for instructing the output of the predicted value of the data to be evaluated and the presentation of the case data.

The output field 1002 displays the predicted value of the data to be evaluated and the interpretation information. In the output field 1002, display data 1031, 1032, and 1033 which are composed of a type 1021, a value 1022, and a basis vector 1023 are displayed.

The type 1021 is a field for displaying identification information of the data. The value 1022 is a field for displaying the predicted value of the data to be evaluated (display data 1031) and displaying the correct answer value or a predicted value of the case data (display data 1032, 1033). The basis vector 1023 is a field for displaying the basis vector. Graphs showing the contribution degree of each item are displayed in the basis vector 1023. The name of each item and the value of the contribution degree of each item may be displayed.

The display data 1031 is display data of information on the data to be evaluated. The display data 1032, 1033 are display data of the case data selected by the case extraction unit 112.

Here, an operation example of the analysis screen 1000 will be described. First, the user sets values in fields 1011, 1012, 1013 of the data setting field 1001. Next, the user operates the execution button 1014. Upon receiving an operation of the user, the terminal 101 transmits a processing execution request including the values set in the data setting field 1001 to the operation receiving unit.

Upon receiving the operation, the operation receiving unit instructs the computers 100-2, 100-3 to execute the processing shown in FIGS. 6 to 9.

In the above operation, the calculation processing of the basis vector of the case data, the output processing of the predicted value of the data to be evaluated, and the selection processing of the case data are performed as a series of processing. As another form, the calculation processing of the basis vector of the case data, the output processing of the predicted value of the data to be evaluated, and the selection processing of the case data are performed separately. In this case, it may be divided into a data setting field including the first data setting field 1011, the second data setting field 1012, and the execution button, and a data setting field including the third data setting field 1013 and the execution button.

According to the first embodiment, the computer system can present, together with the predicted value of the data to be evaluated, the basis vector of the data to be evaluated and the information on the case data selected based on the similarity. The user can grasp the feature emphasized by the predictor 110 based on the basis vector of the evaluation object data, and can recognize the predicted value of the data to be evaluated with a feeling of conviction by referring to the information on the case data.

Second Embodiment

In the second embodiment, the selection criterion of case data is different from that of the first embodiment. Hereinafter, the second embodiment will be described focusing on differences from the first embodiment.

The system configuration of the second embodiment is the same as that of the first embodiment. The hardware configuration and software configuration of a computer 100 according to the second embodiment are the same as those of the first embodiment. Information handled in the second embodiment is the same as that of the first embodiment. Processing executed by a basis vector calculation unit 111 according to the second embodiment is the same as that of the first embodiment.

Figure 11:
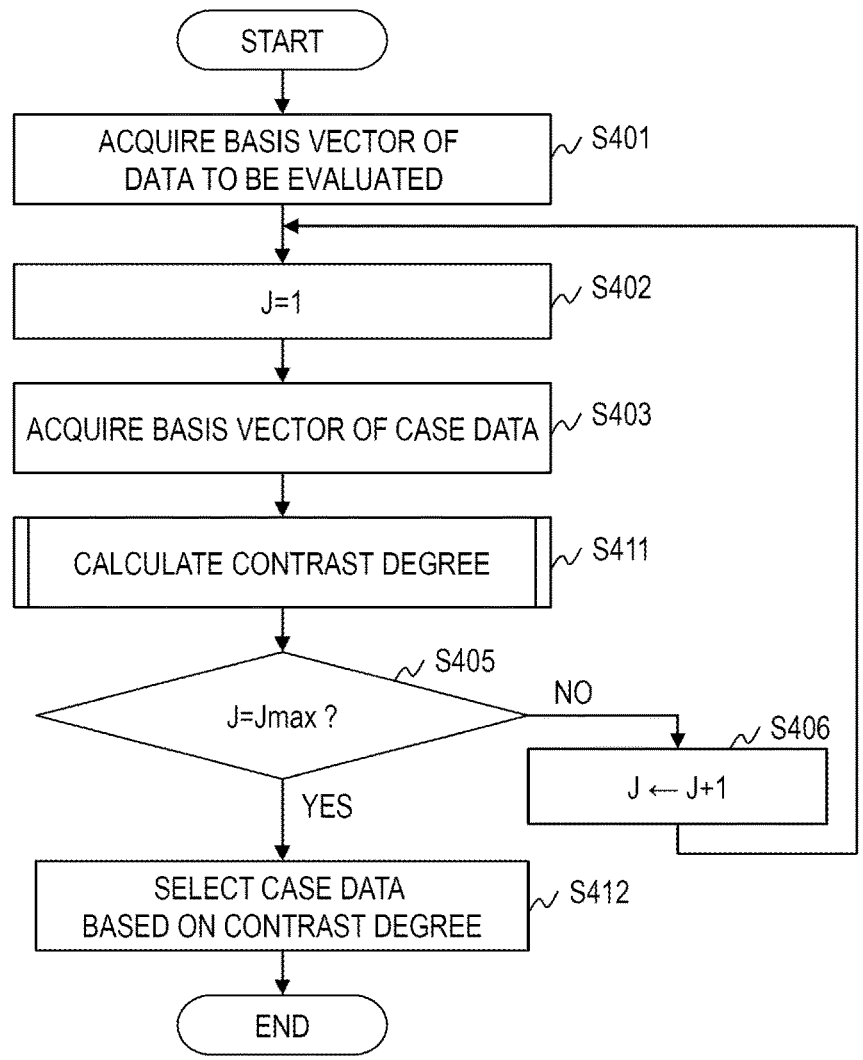
FIG. 11 is a flowchart showing an example of case data selection processing executed by a case extraction unit according to a second embodiment.

In the second embodiment, the processing executed by a case extraction unit 112 is partially different from that of the first embodiment. FIG. 11 is a flowchart showing an example of case data selection processing executed by the case extraction unit 112 according to the second embodiment. FIG. is a flowchart showing an example of contrast degree calculation processing executed by the case extraction unit 112 according to the second embodiment.

Since the processing steps having the same reference numerals in the second embodiment are the same as those in the first embodiment, a description thereof is omitted. After the processing of step S403, the case extraction unit 112 executes contrast degree calculation processing (step S411).

Figure 12:
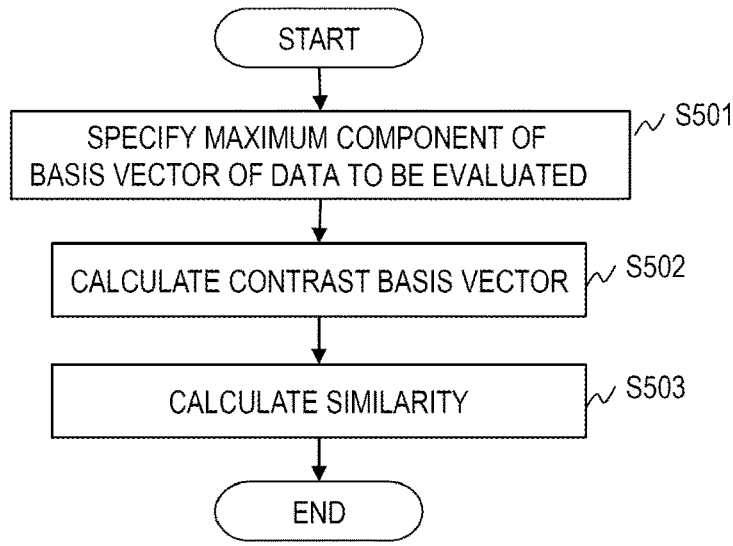
FIG. 12 is a flowchart showing an example of contrast degree calculation processing executed by the case extraction unit according to the second embodiment.

The contrast degree is a selection index for specifying the case data having a feature in contrast with the data to be evaluated in a prediction of a predictor 110. It is indicated that the feature in contrast with the data to be evaluated in the prediction of the predictor 110 is a basis vector with a small contribution to a feature emphasized by the predictor 110. Here, a method of calculating the contrast degree will be described with reference to FIG. 12.

The case extraction unit 112 calculates an absolute value of each component of the basis vector of the data to be evaluated, and specifies a component having the largest absolute value (step S501). In the following description, the specified component is also referred to as a maximum component.

Next, the case extraction unit 112 calculates a contrast basis vector (step S502).

Specifically, the case extraction unit 112 sets the maximum component of the basis vector of the data to be evaluated as 0. Values of the components excluding the largest component are set as the same value. In this way, a condition of a contrast case in which only the maximum component is different can be specified. The vector calculated by the above operations is the contrast basis vector.

Although the calculation method of setting the maximum component as 0 has been described in the present embodiment, variations of other calculation methods can be easily applied. For example, a calculation method of performing the above-described processing for the top two components other than the maximum value, or a calculation method inverting a sign of the maximum component may be considered.

Next, the case extraction unit 112 calculates, as the contrast degree, the similarity between the contrast basis vector and the basis vector of the case data (step S503). The invention is not limited to the above calculation methods of similarity.

The explanation will now return to FIG. 11. When the determination result of step S405 is YES, the case extraction unit 112 selects the case data based on the contrast degree (step S412). Thereafter, the case extraction unit 112 ends the processing.

For example, the case extraction unit 112 selects the case data having the highest contrast degree or the case data having a contrast degree larger than a threshold. In addition, the case extraction unit 112 selects a predetermined number of pieces of the case data in descending order of the contrast degree. The invention is not limited to the method of selecting the case data based on the contrast degree.

According to the second embodiment, by presenting the case data corresponding to the basis vector that does not have the feature of the basis vector of the data to be evaluated, the user can recognize a prediction basis of the predictor 110 with a feeling of conviction.

Third Embodiment

In the third embodiment, a computer 100 executes analysis processing using a basis vector of data to be evaluated and selected case data. Hereinafter, the third embodiment will be described focusing on differences from the first embodiment.

Figure 13:
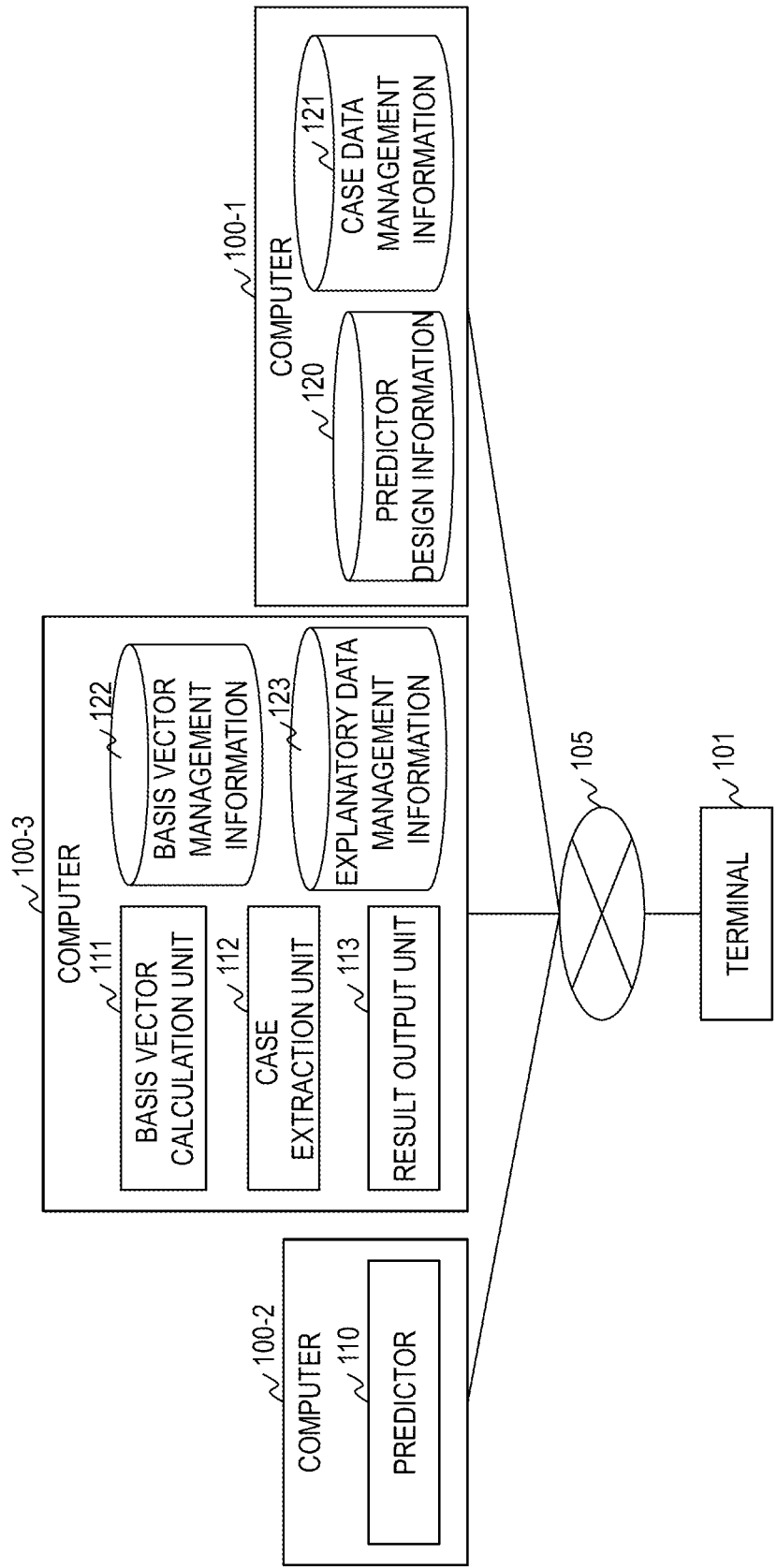
FIG. 13 shows a configuration example of a computer system according to a third embodiment.
Figure 14:
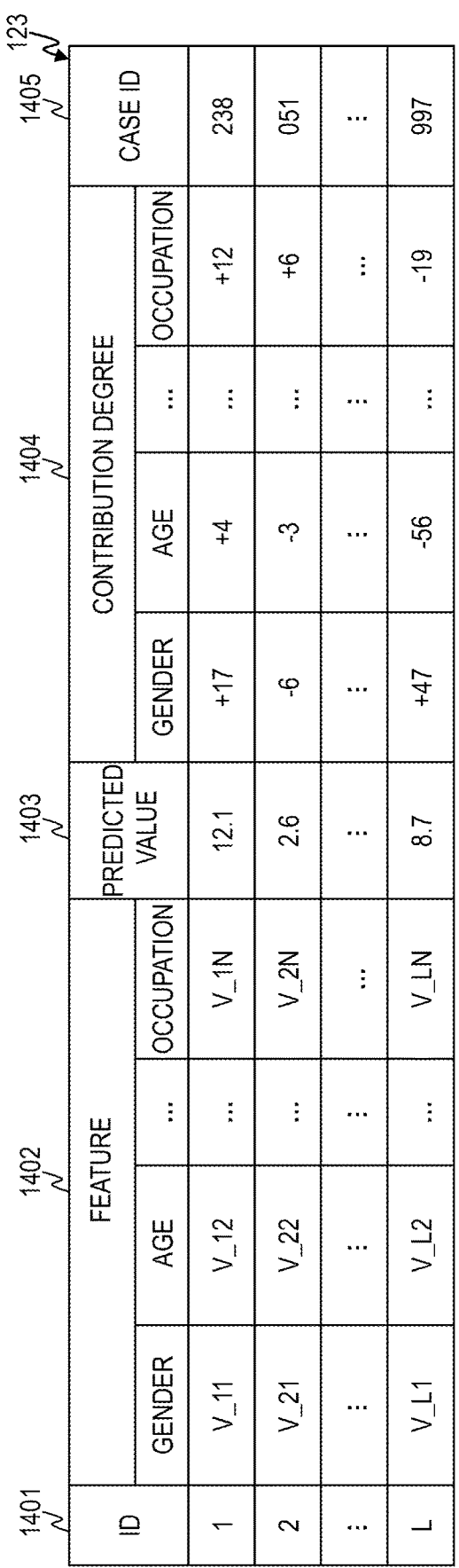
FIG. 14 shows an example of a data structure of explanatory data management information according to the third embodiment.

FIG. 13 shows a configuration example of a computer system according to the third embodiment. FIG. 14 shows an example of a data structure of explanatory data management information 123 according to the third embodiment.

The system configuration of the third embodiment is the same as that of the first embodiment. The hardware configuration of the computer 100 of the third embodiment is the same as that of the first embodiment. The software configurations of computers 100-1, 100-2 according to the third embodiment are the same as those of the first embodiment. In the third embodiment, as shown in FIG. 13, the software configuration of a computer 100-3 is different from that of the first embodiment.

The computer 100-3 according to the third embodiment holds the explanatory data management information 123. Here, the explanatory data management information 123 will be described with reference to FIG. 14.

The explanatory data management information 123 stores entries including an ID 1401, a feature 1402, a predicted value 1403, a contribution degree 1404, and a case ID 1405. One entry corresponds to one piece of description data. As described below, one piece of description data is generated with respect to one piece of data to be evaluated.

The ID 1401 is a field for storing identification information of the data to be evaluated. The feature 1402 is a field group for storing a feature of each item of the data to be evaluated. The predicted value 1403 is a field for storing a predicted value obtained by inputting the feature to a predictor 110. The contribution degree 1404 is a field group for storing a contribution degree to the predicted value 1403 for the feature of each item of the data to be evaluated. The case ID 1405 is a field for storing identification information of the case data selected by the case data selection processing.

Data structures of predictor design information 120, case data management information 121, and basis vector management information 122 of the third embodiment are the same as those of the first embodiment. Processing executed by a basis vector calculation unit 111 of the third embodiment is the same as that of the first embodiment.

However, in the third embodiment, since a plurality of pieces of data to be evaluated are input, the predictor 110 outputs the predicted value of each of a plurality of pieces of data to be evaluated, and the basis vector calculation unit 111 calculates the basis vector of each of a plurality of pieces of data to be evaluated. At this time, the basis vector calculation unit 111 temporarily stores, in a storage area, the basis vector corresponding to the identification information of the data to be evaluated.

In the third embodiment, processing executed by a case extraction unit 112 is different from that of the first embodiment.

Figure 15:
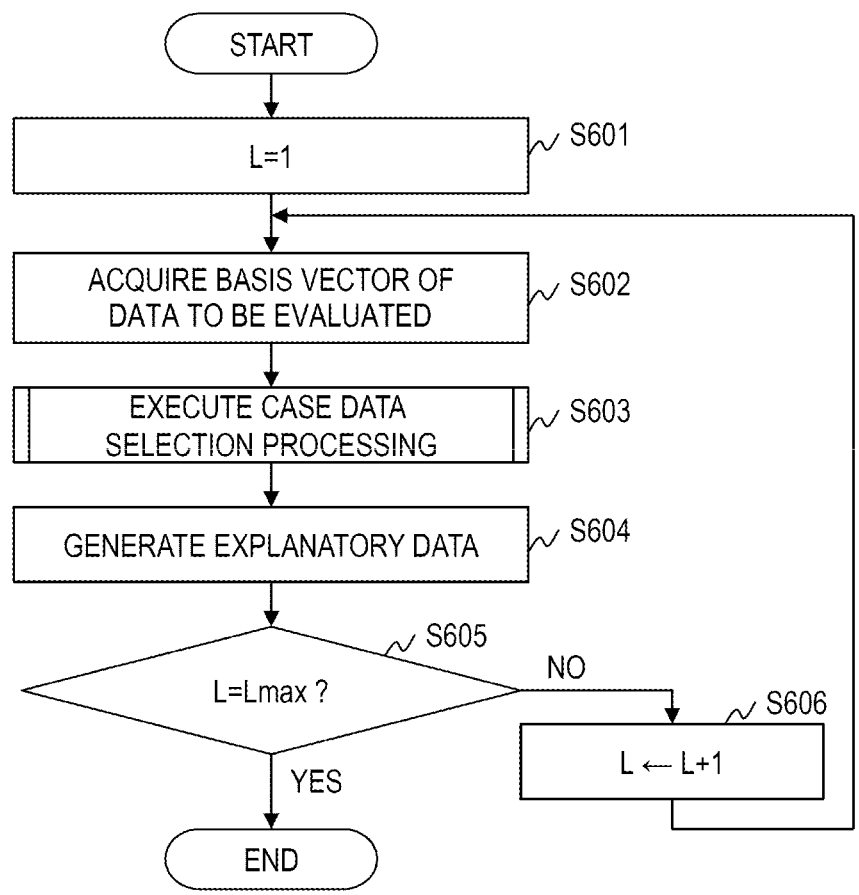
FIG. 15 is a flowchart showing an example of generation processing of the explanatory data management information executed by a case extraction unit according to the third embodiment.

FIG. 15 is a flowchart showing an example of generation processing of the explanatory data management information 123 executed by the case extraction unit 112 according to the third embodiment.

Upon receiving a generation instruction of the explanatory data management information 123, the case extraction unit 112 starts the processing described below. The generation instruction of the explanatory data management information 123 includes a plurality of pieces of data to be evaluated.

The case extraction unit 112 sets "1" as the initial value of a variable L (step S601). The variable L represents the identification number of the data to be evaluated. At this time, the case extraction unit 112 sets the number of pieces of the data to be evaluated as Lmax.

Next, the case extraction unit 112 acquires the basis vector of the data to be evaluated corresponding to the variable L from the storage area (step S602).

Next, the case extraction unit 112 executes case data selection processing on the data to be evaluated corresponding to the variable L (step S603). The case data selection processing may be applied to anyone of FIGS. 9 and 11.

Next, the case extraction unit 112 generates explanatory data of the data to be evaluated corresponding to the variable L (step S604).

Specifically, the case extraction unit 112 generates the explanatory data by combining the identification information of the data to be evaluated, the feature of the data to be evaluated, the predicted value of the data to be evaluated, the contribution degree of the feature of the data to be evaluated, and the identification information of the selected case data. In addition, the case extraction unit 112 adds an entry to the explanatory data management information 123, and registers the generated explanatory data in the added entry.

Next, the case extraction unit 112 determines whether the value of the variable L is identical to Lmax (step S605). That is, it is determined whether the processing is executed for all the data to be evaluated.

When it is determined that the value of the variable L is not identical to Lmax, the case extraction unit 112 sets a value obtained by adding 1 to the value of the variable L as the variable L (step S606). Thereafter, the processing returns to step S602 and the case extraction unit 112 executes the same processing.

When it is determined that the value of the variable L is identical to Lmax, the case extraction unit 112 ends the processing. At this time, the case extraction unit 112 notifies, via an operation receiving unit, a terminal 101 that the explanatory data management information 123 is generated.

Figure 16:
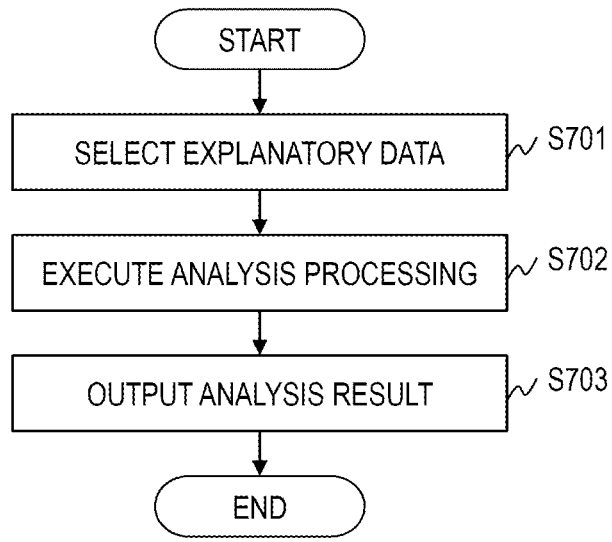
FIG. 16 is a flowchart showing an example of analysis processing executed by the case extraction unit according to the third embodiment.

FIG. 16 is a flowchart showing an example of analysis processing executed by the case extraction unit 112 according to the third embodiment.

Upon receiving an execution instruction of the analysis processing, the case extraction unit 112 starts the processing described below. The execution instruction of the analysis processing includes setting information of filtering of the explanatory data. When it is not necessary to narrow down the explanatory data, the setting information of filtering of the explanatory data may not be included in the execution instruction of the analysis processing.

First, the case extraction unit 112 selects the explanatory data (step S701). Since the data selection method based on the setting information of filtering is a well-known technique, a detailed description thereof is omitted.

Next, the case extraction unit 112 executes the analysis processing using the selected explanatory data (step S702). In the third embodiment, the following analysis processing is executed.

(Analysis processing of feature tendency) The case extraction unit 112 analyzes the tendency of the feature of the item that is important in the predicted value of the data to be evaluated. Specifically, the case extraction unit 112 analyzes the distribution of the features of a component having a large value of the contribution degree 1404. The case extraction unit 112 outputs an analysis result as ranking data.

(Analysis processing of reference tendency of case data) The case extraction unit 112 aggregates the case data selected by the case data selection processing. Specifically, the case extraction unit 112 calculates the number of times of selection of the case data as the number of times of reference, based on the case ID 1405 of the selected explanatory data. In addition, the case extraction unit 112 calculates the appearance proportion of the case data as a reference proportion, based on the number of times of reference.

Next, the case extraction unit 112 outputs the analysis result to a result output unit 113 (step S703), and ends the processing.

The result output unit 113 according to the third embodiment transmits display information including the analysis result as interpretation information to the terminal 101. The result output unit 113 according to the third embodiment may not transmit the predicted value of the data to be evaluated.

Figure 17A:
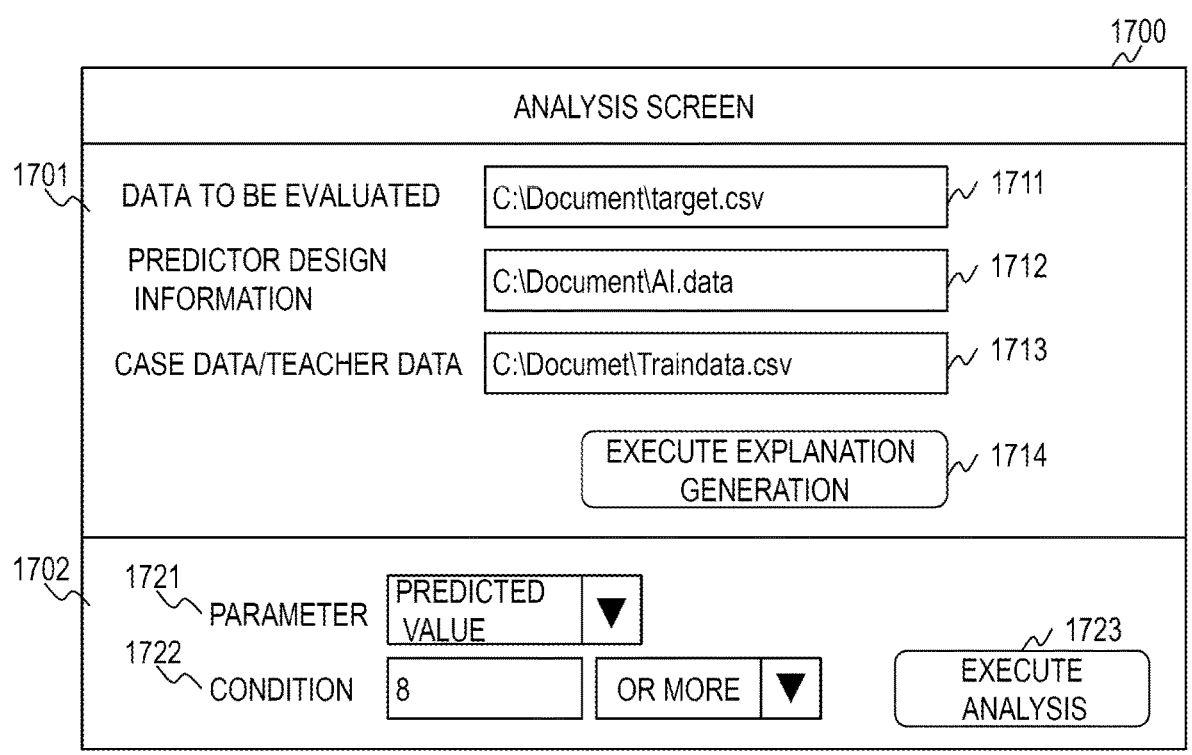
FIG. 17A shows an example of an analysis screen displayed on a terminal according to the third embodiment.
Figure 17B:
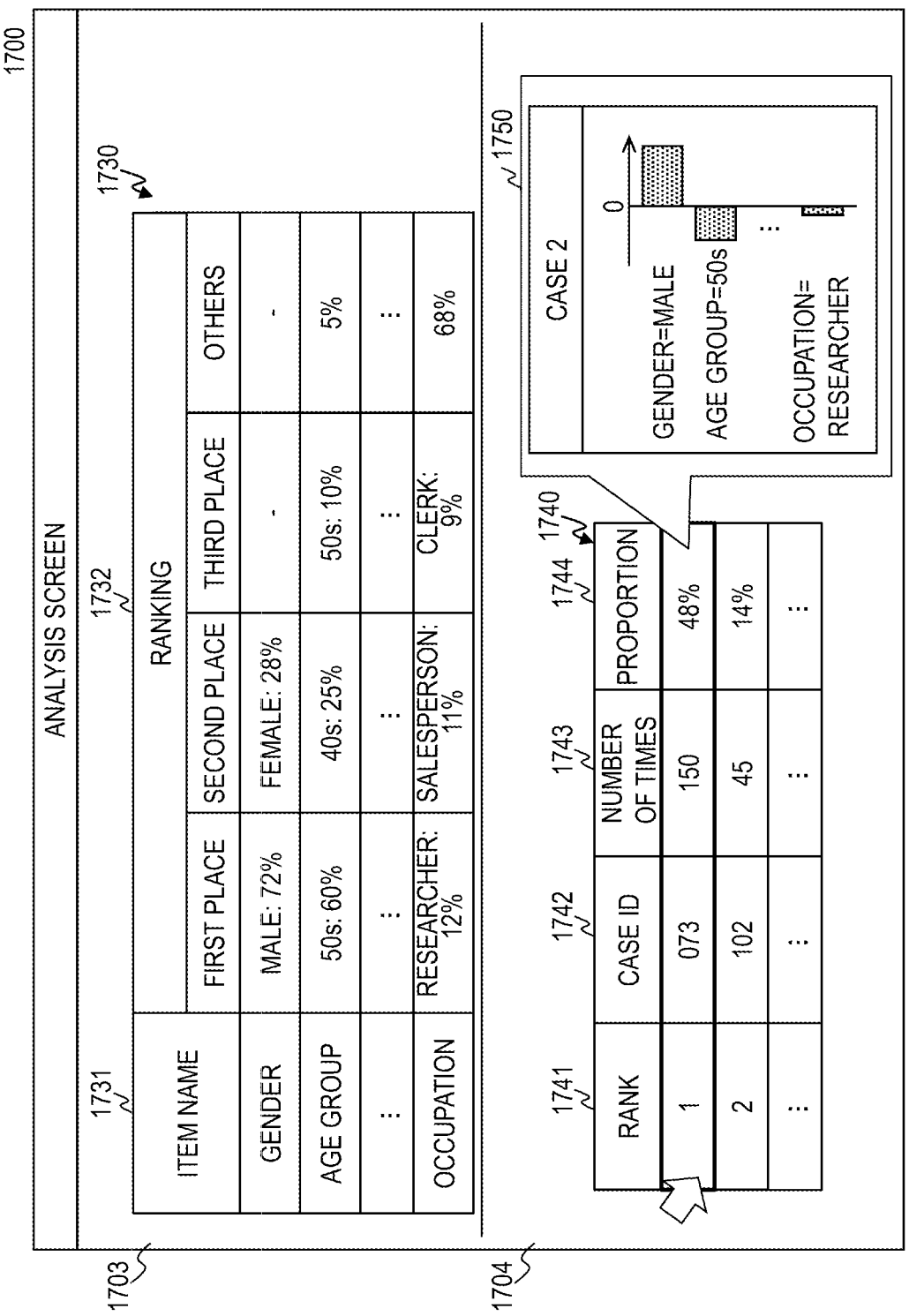
FIG. 17B shows an example of an analysis screen displayed on the terminal according to the third embodiment.

FIGS. 17A, 17B, and 17C respectively show an example of an analysis screen displayed on the terminal 101 according to the third embodiment.

An analysis screen 1700 is provided by the operation receiving unit and is displayed on the terminal 101. The analysis screen 1700 includes a field for setting data to be used in the processing and a field for displaying the result of the analysis processing.

First, the field for setting the data to be used in the processing will be described with reference to FIG. 17A. The analysis screen 1000 includes a data setting field 1701 and a filtering setting field 1702 as fields for setting the data to be used in the processing.

The data setting field 1701 is the same as the data setting field 1001. However, in the third embodiment, when an execution button 1714 is operated, the terminal 101 transmits a generation request of the explanatory data management information 123 to the operation receiving unit.

The filtering setting field 1702 is a field for setting filtering. The filtering setting field 1702 includes a parameter setting field 1721, a condition setting field 1722, and an execution button 1723.

The parameter setting field 1721 is a field for setting the type of the parameter serving as a selection criterion. The condition setting field 1722 is a field for setting the range of the parameter. The execution button 1723 is an operation button for instructing execution of the analysis processing. When the execution button 1723 is operated, the terminal 101 transmits an execution request of the analysis processing to the operation receiving unit.

Next, a field for displaying the result of the analysis processing will be described with reference to FIGS. 17B and 17C. The analysis screen 1700 includes a feature analysis field 1703 and a case data analysis column 1704 as fields for displaying the result of the analysis processing.

The feature analysis field 1703 displays the result of the analysis processing of the feature tendency and includes feature analysis information 1730. The feature analysis information 1730 includes an entry composed of an item name 1731 and a ranking 1732. One entry corresponds to a component of the data to be evaluated.

The item name 1731 is a field for storing identification information of an item of the data to be evaluated.

The ranking 1732 is a field for displaying the ranking of the feature set in the item corresponding to the item name 1731 and includes fields of "first place", "second place", "third place", and "others".

In the fields of "first place", "second place", and "third place", combinations of features and proportions of the data to be evaluated in which the features are set are stored. In the "Others" field, proportions of the data to be evaluated in which features other than the features stored in the "first place", "second place", and "third place" fields are set are stored.

In FIG. 17C, for the sake of concise explanation, details of the feature analysis information 1730 are omitted.

The case data analysis field 1704 displays the result of the analysis processing of the reference tendency of the case data. FIG. 17B shows a display example when filtering is performed. FIG. 17C shows a display example when filtering is not performed.

The case data analysis field 1704 of FIG. 17B includes case analysis information 1740. The case analysis information 1740 stores entries which are a rank 1741, a case ID 1742, a number of times 1743, and a proportion 1744. One entry corresponds to one piece of case data. The entries stored in the case analysis information 1740 are sorted in descending order of the number of times of reference.

The rank 1741 is a field for storing a rank based on the number of times of reference. The case ID 1742 is a field for storing identification information of the case data. The number of times 1743 is a field for storing the number of times of selecting the case data corresponding to the case ID 1742 in the case data selection processing. The proportion 1744 is a field for storing the proportion of the number of times of selection of the case data in the total value of the number of times of selection of each piece of case data.

In a case where a user selects the entry of the case analysis information 1740, the basis vector or the like of the case data corresponding to the selected entry is displayed as a balloon display 1750.

The case data analysis field 1704 in FIG. 17C displays the case analysis information 1740. The case analysis information 1740 stores entries which are the rank 1741, the case ID 1742, the number of times 1743, the proportion 1744, a graph 1745, and a cumulative proportion 1746. One entry corresponds to one piece of case data. The entries stored in the case analysis information 1740 are sorted in descending order of the number of times of reference.

The graph 1745 is a field for displaying a graph for visually displaying the proportion 1744. The cumulative proportion 1746 is a field for storing the cumulative value of the proportion 1744. For example, the total value of the proportion 1744 of each entry from "1" to "j−1" in the rank 1741 is stored in the cumulative proportion 1746 of an entry of which the rank 1741 is "j".

According to the third embodiment, by displaying the result of the analysis based on the basis vector of each predicted value of the plurality of pieces of the data to be evaluated, the user can grasp useful case data from the statistical viewpoint and can grasp the tendency of the important feature in the prediction of the predictor 110.

It should be noted that the invention is not limited to the above-described embodiments and includes various modifications. For example, the embodiments described above are described in detail for easy understanding but the invention is not necessarily limited to those including all the above configurations. Apart of the configuration of each embodiment may be added, deleted, or replaced with another configuration.

In regard to each of the above-mentioned configurations, functions, processing units, processing methods, and the like, a part thereof or an entirety thereof may be achieved by hardware, for example, by being designed as an integrated circuit. In addition, the invention can be achieved by a program code of software realizing the functions of the embodiments. In this case, a storage medium that stores the program code is provided to a computer, and a processor included in the computer reads out the program code stored in the storage medium. In this case, the program code itself read out from the storage medium realizes the functions of the above embodiments, and the program code itself and the storage medium storing the program code constitute the invention. The storage medium for supplying the program code includes, such as a flexible disk, a CD-ROM, a DVD-ROM, a hard disk, a Solid State Drive (SSD), an optical disk, a magneto-optical disk, a CD-R, a magnetic tape, a nonvolatile memory card, and a ROM.

For example, the program code that realizes the function described in this embodiment can be realized by a wide range of programs or scripting languages, such as an assembler, C/C++, perl, Shell, PHP, and Java (registered trademark).

Further, by distributing the program code of the software realizing the functions of the embodiments through a network, the program code is stored in a storage unit such as the hard disk or the memory of the computer or in a storage medium such as a CD-RW or the CD-R. The processor included in the computer may read out and execute the program code stored in the storage unit or the storage medium.

In the above-described embodiments, only control lines and information lines that are considered necessary for description are illustrated, and not necessarily all the control lines and information lines required for production are illustrated. All of the configurations may be mutually connected.

What is claimed is:

1. A computer system that outputs a predicted value of data to be evaluated composed of a plurality of features using a predictor generated using a plurality of pieces of learning data composed of the plurality of features and correct answer values,
the computer system comprising:
at least one computer including a processor, a memory connected to the processor, and a network interface connected to the processor;
the predictor;
an index calculation unit that calculates a first interpretation index configured to interpret the predicted value of the data to be evaluated output by the predictor; and
an extraction unit that calculates a selection index configured to select the learning data useful for a user to interpret the predicted value of the data to be evaluated, and selects the learning data based on the selection index, wherein
index management information configured to manage a second interpretation index configured to interpret the correct answer value included in the learning data is stored,
the predictor outputs the predicted value of the data to be evaluated,
the index calculation unit calculates the first interpretation index based on the data to be evaluated and the predicted value of the data to be evaluated, and
the extraction unit calculates the selection index based on the first interpretation index and the second interpretation index, selects the learning data based on the selection index, generates display information configured to present information on the interpretation index of the data to be evaluated and the selected learning data, ands output the display information.

2. The computer system according to claim 1, wherein
the first interpretation index is a basis vector having a contribution degree to the predicted value of each of the plurality of features constituting the data to be evaluated, and
the second interpretation index is a basis vector having a contribution degree to the correct answer value of each of the plurality of features constituting the learning data.

3. The computer system according to claim 2, wherein
the extraction unit calculates, as the selection index, a similarity between a basis vector of the data to be evaluated and a basis vector of the learning data.

4. The computer system according to claim 2, wherein
the extraction unit is configured to:
calculate a contrast basis vector having a feature in contrast with the basis vector of the data to be evaluated using the basis vector of the data to be evaluated, and
calculate, as the selection index, the similarity between the contrast basis vector and the basis vector of the learning data.

5. The computer system according to claim 3, wherein
the predictor outputs the predicted value of each of the plurality of pieces of the data to be evaluated,
the index calculation unit calculates the first interpretation index of each of the plurality of pieces of the data to be evaluated, and
the extraction unit is configured to:
calculate the selection index of each of the plurality of pieces of the data to be evaluated,
select the learning data of each of the plurality of pieces of the data to be evaluated based on the selection index of the data to be evaluated,
perform analysis processing using the plurality of pieces of the data to be evaluated and the selected learning data, and
generate the display information including a result of the analysis processing.

6. The computer system according to claim 5, wherein
the result of the analysis processing includes at least one of information on a tendency of the feature and information on the number of times of selection as the learning data presented by the extraction unit.

7. A method of presenting information related to a basis of a predicted value output by a predictor, being executed by a computer system that outputs a predicted value of data to be evaluated composed of a plurality of features using the predictor generated using a plurality of pieces of learning data composed of a plurality of features and correct answer values, wherein
the computer system includes at least one computer including a processor, a memory connected to the processor, and a network interface connected to the processor,
includes the predictor, an index calculation unit that calculates a first interpretation index configured to interpret the predicted value of the data to be evaluated output by the predictor, and an extraction unit that calculates a selection index configured to select the learning data useful for a user to interpret the predicted value of the data to be evaluated and selects the learning data based on the selection index, and
stores index management information configured to manage a second interpretation index configured to interpret the correct answer value included in the learning data, the method of presenting information related to the basis of the predicted value output by the predictor comprising:
a first step in which the predictor outputs the predicted value of the data to be evaluated;
a second step in which the index calculation unit calculates the first interpretation index based on the predicted value of the data to be evaluated and the data to be evaluated;

a third step in which the extraction unit calculates the selection index based on the first interpretation index and the second interpretation index;

a fourth step in which the extraction unit selects the learning data based on the selection index; and a fifth step in which the extraction unit generates display information configured to present information on the interpretation index of the data to be evaluated and the selected learning data and outputs the display information.

8. The method of presenting information related to the basis of the predicted value output by the predictor according to claim 7, wherein the first interpretation index is a basis vector having a contribution degree to the predicted value of each of the plurality of features constituting the data to be evaluated, and the second interpretation index is a basis vector having a contribution degree to the correct answer value of each of the plurality of features constituting the learning data.

9. The method of presenting information related to the basis of the predicted value output by the predictor according to claim 8, wherein the third step includes a step in which the extraction unit calculates, as the selection index, a similarity between a basis vector of the data to be evaluated and a basis vector of the learning data.

10. The method of presenting information related to the basis of the predicted value output by the predictor according to claim 8, wherein the third step includes a step in which the extraction unit calculates a contrast basis vector having a feature in contrast with the basis vector of the data to be evaluated using the basis vector of the data to be evaluated, and a step in which the extraction unit calculates, as the selection index, a similarity between the contrast basis vector and the basis vector of the learning data.

11. The method of presenting information related to the basis of the predicted value output by the predictor according claim 9, wherein the first step includes a step in which the predictor outputs the predicted value of each of a plurality of pieces of the data to be evaluated, the second step includes a step in which the index calculation unit calculates the first interpretation index of each of the plurality of pieces of the data to be evaluated, the third step includes a step in which the extraction unit calculates the selection index of each of the plurality of pieces of the data to be evaluated, the fourth step includes a step in which the extraction unit selects the learning data of each of the plurality of pieces of the data to be evaluated based on the selection index of the data to be evaluated, and the fifth step includes a step in which the extraction unit performs analysis processing using the plurality of pieces of the data to be evaluated and the selected learning data and a step in which the extraction unit generates the display information including a result of the analysis processing.

12. The method of presenting information related to the basis of the predicted value output by the predictor according to claim 11, wherein the result of the analysis processing includes at least one of information on a tendency of the feature and information on the number of times of selection as the learning data presented by the extraction unit.

* * * * *